(12) United States Patent
Burgermeister

(10) Patent No.: US 7,351,214 B2
(45) Date of Patent: Apr. 1, 2008

(54) STEERABLE BALLOON CATHETER

(75) Inventor: Robert Burgermeister, Bridgewater, NJ (US)

(73) Assignee: Cordis Corporation, Miami Lakes, FL (US)

( * ) Notice: Subject to any disclaimer, the term of this patent is extended or adjusted under 35 U.S.C. 154(b) by 391 days.

(21) Appl. No.: 10/691,824

(22) Filed: Oct. 23, 2003

(65) Prior Publication Data
US 2004/0193205 A1 Sep. 30, 2004

Related U.S. Application Data

(63) Continuation-in-part of application No. 10/224,168, filed on Aug. 20, 2002, now Pat. No. 7,128,718.

(60) Provisional application No. 60/366,739, filed on Mar. 22, 2002.

(51) Int. Cl.
A61B 5/00 (2006.01)
A61B 6/00 (2006.01)
A61B 8/00 (2006.01)
A61M 25/00 (2006.01)
A61M 31/00 (2006.01)
A61M 37/00 (2006.01)
A61M 29/00 (2006.01)
A61M 5/178 (2006.01)
A61M 5/00 (2006.01)

(52) U.S. Cl. ............... 600/585; 604/103.09; 604/103; 604/95.01; 604/525; 604/530; 604/264; 604/508; 604/509; 604/95.03; 604/96.01; 604/97.01; 604/98.01; 604/99.01; 604/104; 604/164.03; 604/164.13; 604/528; 600/453; 600/434; 600/435; 600/433

(58) Field of Classification Search ............... 600/585, 600/453, 434, 435, 433, 549; 604/103.09, 604/103, 95.01, 525, 530, 264, 508, 509, 604/95.03, 96.01, 97.01, 98.01, 99.01, 104, 604/164.03, 164.13, 528, 6.13, 290
See application file for complete search history.

(56) References Cited

U.S. PATENT DOCUMENTS 4,003,369 A 1/1977 Heilman et al.
4,665,906 A 5/1987 Jervis (Continued)

FOREIGN PATENT DOCUMENTS

EP 0274412 B1 7/1988

(Continued)

OTHER PUBLICATIONS

European Search Report dated Sep. 2, 2005 for European Patent Application No. 04256553.1 And European Search Report dated Jan. 6, 2006 for European Patent Application No. 04256537.4.

*Primary Examiner*—Max F. Hindenburg
*Assistant Examiner*—Jeff Hoekstra

(57) ABSTRACT

A steerable balloon catheter including a balloon catheter supported by a steerable guidewire having a deflectable distal tip. The guidewire comprises a longitudinal hypotube and a spring coil attached to the distal end of the hypotube and includes a longitudinally movable deflection member which is attached to the distal end of the spring coil and a tip retaining member which extends from the distal end of the hypotube to the distal end of the spring coil for providing very precise deflection of the distal tip of the balloon catheter.

30 Claims, 5 Drawing Sheets

U.S. PATENT DOCUMENTS

| | | | |
|---|---|---|---|
| 4,719,924 A | 1/1988 | Crittenden et al. | |
| 4,757,827 A | 7/1988 | Buchbinder et al. | |
| 4,770,188 A | 9/1988 | Chikama | |
| 4,813,434 A | 3/1989 | Buchbinder et al. | |
| 4,815,478 A | 3/1989 | Buchbinder et al. | |
| 4,827,941 A | 5/1989 | Taylor et al. | |
| 4,854,325 A | 8/1989 | Stevens | |
| 4,875,489 A | 10/1989 | Messner et al. | |
| 4,881,981 A | 11/1989 | Thoma et al. | |
| 4,886,067 A | 12/1989 | Palermo | |
| 4,921,482 A | 5/1990 | Hammerslag et al. | |
| 4,923,462 A | 5/1990 | Stevens | |
| 4,925,445 A | 5/1990 | Sakamoto et al. | |
| 4,935,068 A | 6/1990 | Duerig | |
| 4,935,088 A | 6/1990 | Mitsuyama | |
| 4,936,845 A | 6/1990 | Stevens | |
| 4,940,062 A * | 7/1990 | Hampton et al. | 600/585 |
| 4,953,553 A | 9/1990 | Tremulis | |
| 4,966,163 A | 10/1990 | Kraus et al. | |
| 4,984,581 A | 1/1991 | Stice | |
| 4,998,916 A | 3/1991 | Hammerslag et al. | |
| 5,037,391 A | 8/1991 | Hammerslag et al. | |
| 5,060,660 A | 10/1991 | Gambale et al. | |
| 5,069,226 A | 12/1991 | Yamauchi et al. | |
| 5,078,722 A | 1/1992 | Stevens | |
| 5,116,350 A | 5/1992 | Stevens | |
| 5,120,308 A | 6/1992 | Hess | |
| 5,125,395 A | 6/1992 | Adair | |
| 5,133,364 A | 7/1992 | Palermo et al. | |
| 5,143,085 A | 9/1992 | Wilson | |
| 5,159,937 A | 11/1992 | Tremulis | |
| 5,188,621 A | 2/1993 | Samson | |
| 5,190,050 A | 3/1993 | Nitzsche | |
| 5,203,772 A | 4/1993 | Hammerslag et al. | |
| 5,242,394 A | 9/1993 | Tremulis | |
| 5,341,818 A | 8/1994 | Abrams et al. | |
| 5,365,942 A | 11/1994 | Shank | |
| 5,368,049 A | 11/1994 | Raman et al. | |
| 5,372,587 A | 12/1994 | Hammerslag et al. | |
| 5,397,305 A | 3/1995 | Kawula et al. | |
| 5,480,382 A | 1/1996 | Hammerslag et al. | |
| 5,501,694 A | 3/1996 | Ressemann et al. | |
| 5,682,899 A * | 11/1997 | Nashef et al. | 600/505 |
| 5,695,111 A | 12/1997 | Nanis et al. | |
| 5,807,279 A | 9/1998 | Viera | |
| 5,813,997 A | 9/1998 | Imran et al. | |
| 5,882,333 A * | 3/1999 | Schaer et al. | 604/95.01 |
| 5,891,055 A | 4/1999 | Sauter | |
| 5,908,405 A * | 6/1999 | Imran et al. | 604/508 |
| 5,931,830 A | 8/1999 | Jacobsen et al. | |
| 6,027,460 A | 2/2000 | Shturman | |
| 6,059,739 A | 5/2000 | Baumann | |
| 6,126,649 A | 10/2000 | VanTassel et al. | |
| 6,146,338 A | 11/2000 | Gardeski et al. | |
| 6,193,706 B1 | 2/2001 | Thorud et al. | |
| 6,273,876 B1 | 8/2001 | Klima et al. | |
| 6,306,105 B1 | 10/2001 | Rooney et al. | |
| 6,352,515 B1 | 3/2002 | Anderson et al. | |
| 6,355,016 B1 * | 3/2002 | Bagaoisan et al. | 604/103.09 |
| 6,375,628 B1 | 4/2002 | Zadno-Azizi et al. | |
| 6,379,369 B1 | 4/2002 | Abrams et al. | |
| 6,468,230 B2 | 10/2002 | Muni et al. | |
| 6,488,637 B1 | 12/2002 | Eder et al. | |
| 2002/0019599 A1 | 2/2002 | Rooney et al. | |
| 2002/0038129 A1 | 3/2002 | Peters et al. | |
| 2002/0049392 A1 | 4/2002 | DeMello | |
| 2002/0151966 A1 | 10/2002 | Eder et al. | |
| 2002/0165534 A1* | 11/2002 | Hayzelden et al. | 606/41 |
| 2003/0105415 A1 | 6/2003 | Mirigian | |
| 2004/0068201 A1* | 4/2004 | Saul | 600/561 |
| 2005/0090761 A1* | 4/2005 | Carney | 600/549 |

FOREIGN PATENT DOCUMENTS

| | | |
|---|---|---|
| EP | 0 377 269 B1 | 2/1993 |
| EP | 0778038 B1 | 6/2006 |
| EP | 1346747 B1 | 8/2006 |
| WO | WO 03/051446 A1 | 6/2003 |

* cited by examiner

STEERABLE BALLOON CATHETER

CROSS-REFERENCE TO RELATED APPLICATIONS(S)

This patent application is a continuation-in-part of U.S. patent application Ser. No. 10/224,168, filed on Aug. 20, 2002 now U.S. Pat. No. 7,128,718, entitled, "Guidewire With Deflectable Tip," which is a nonprovisional patent application of U.S. patent application Ser. No. 60/366,739, filed on Mar. 22, 2002, entitled, "Deflection Wire Concept."

BACKGROUND OF THE INVENTION

1. Field of the Invention

The present invention relates to a steerable balloon catheter, and more particularly to a balloon on a bi-directional steerable guidewire having a tip which may be very precisely "steered" and deflected. The guidewire supported balloon is particularly suitable for insertion into a vessel of the body and may be used for angioplasty and/or for placement of a stent within the vessel.

2. Description of the Prior Art

For many years balloons have been mounted on guidewires having a core wire with the distal end being tapered and with a coil spring mounted on the tapered distal end. These guidewires have been used to support and facilitate the insertion of a balloon into a vessel of the body. Generally, the guidewire supported balloon is inserted through a guiding catheter is then moved through the vessel until the balloon is positioned at a desired location.

While most guidewires used to support balloons do not include a mechanism for deflecting or "steering" the tip of the guidewire, it is very desirable to provide tip steering in order to facilitate movement of the balloon through the tortuous vessels of the body. There are many patents directed toward different mechanisms for deflecting the distal tip of a guidewire in order to steer the guidewire. Examples of such guidewires are disclosed in the following patents: U.S. Pat. No. 4,815,478 to Maurice Buchbinder, et al., U.S. Pat. No. 4,813,434 to Maurice Buchbinder, et al., U.S. Pat. No. 5,037,391 to Julius G. Hammerslag, et al., U.S. Pat. No. 5,203,772 to Gary R. Hammerslag, et al., U.S. Pat. No. 6,146,338 to Kenneth C. Gardeski, et al., U.S. Pat. No. 6,126,649 to Robert A. VanTassel, et al., U.S. Pat. No. 6,059,739 to James C. Baumann and U.S. Pat. No. 5,372,587 to Julius G. Hammerslag, et al. U.S. Pat. No. 4,940,062 to Hilary J. Hampton, et al., discloses a balloon catheter having a steerable tip section. All of the above-identified patents are incorporated herein by reference.

While each of this group of patents disclose guidewires which could be used to support a balloon and each having some degree of steerability, there is a need to have a guidewire with very precise "steering" through a vessel of the body. More particularly, there is an important need for a very small diameter guidewire supported balloon having a distal tip which may be rotated and then deflected very precisely to enhance "steerability."

SUMMARY OF THE INVENTION

In accordance with one aspect of the present invention, there is provided a very small diameter steerable balloon catheter having a deflectable tip which includes an elongated flexible guidewire tubing, an outer tubing surrounding the guidewire tubing, an inflatable balloon mounted on the other tubing and communicating with a lumen between the outer tubing and the guidewire tubing. A flexible helical coil is attached to the distal portion of the flexible tubing and an elongated deflection member is slidably disposed within the tubing and within the helical coil. The flexible helical coil is formed from an elongated member having a rectangular, or square cross section, and having continuous undulations wherein the undulations of adjacent turns interlock with each other, i.e., peak undulation of one turn interlocking with valley undulation of adjacent turn, to thereby enhance the rotational rigidity, referred to as "torque" characteristic, of the coil. The proximal portion of the deflection member is of a cylindrical configuration and the distal portion is tapered to form a deflection ribbon. Alternatively, the deflection member may take the form of a proximal cylindrical wire which is attached at its distal end to a deflection ribbon. In addition, a retaining ribbon is attached to the distal end of the flexible tubing and is oriented to extend in a plane which is generally parallel to the plane of the ribbon portion of the deflection member. An attachment member which may take the form of a rounded bead, preferably formed from epoxy, is bonded to the distal end of the helical coil, the distal end of the deflection ribbon and the distal end of the retaining ribbon so that longitudinal movement of the deflection member causes the distal end of the helical coil to be deflected. With the enhanced rotational rigidity of the coil portion or the guidewire, the entire balloon catheter has enhanced rotational rigidity.

In accordance with another aspect of the present invention, the continuous undulations take the form of a sinusoidal wave, or alternatively a square sinusoidal wave, having positive and negative peaks and in which the positive peaks of adjacent turns of coils engage negative peaks, or valleys, of adjacent turns.

In accordance with another aspect of the present invention, the retaining ribbon and the deflection ribbon are preferably pre-shaped into a curved configuration to thereby cause the flexible helical coil to be biased into a normally curved shape.

In accordance with a further aspect of the present invention, the distal portion of the deflection ribbon engages the attachment member, or rounded bead, at a location offset from the center of the attachment member, and the distal portion of the retaining ribbon engages the attachment member at a location offset from the center of the attachment member. Preferably, the retaining ribbon engages the attachment member at a location offset from the center portion of the attachment member in the opposite direction from the offset location of the deflection ribbon.

In accordance with still another aspect of the present invention, the deflection ribbon and the retaining ribbon are connected to each other within the attachment member. Preferably these two elements are formed as a single unitary element. In a preferred embodiment of the invention the cylindrical deflection member is flattened to form the deflection ribbon and is further flattened at its distal end to form the retaining ribbon. The retaining ribbon is bent 180 degrees with respect to the deflection ribbon to form a generally U-shaped bend to thereby establish a predetermined spacing between the ribbons and to also cause these ribbons to remain parallel to each other.

DESCRIPTION OF THE PREFERRED EMBODIMENT

Figure 1:
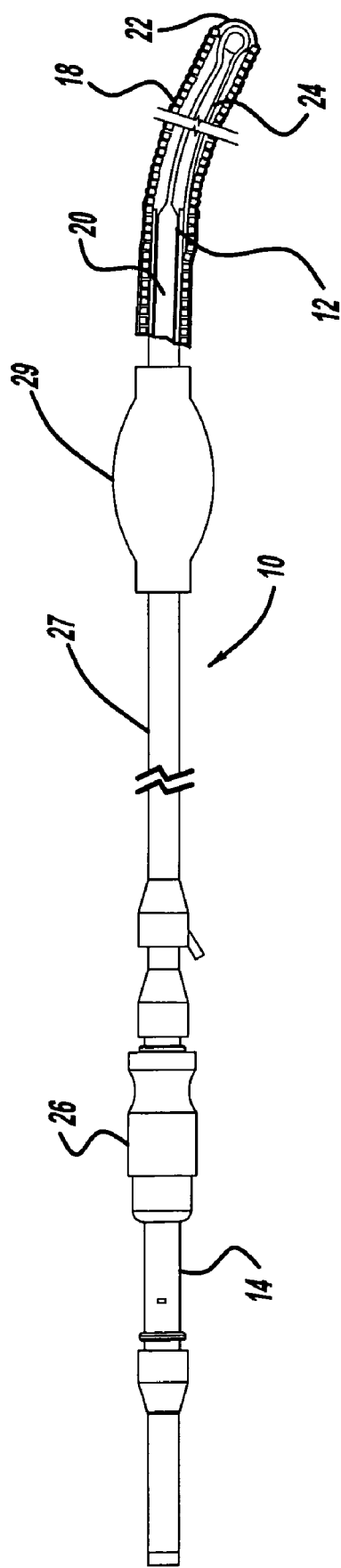
FIG. 1 is an enlarged elevational view of a steerable balloon catheter having a deflectable tip and control handle in accordance with the one aspect of the present invention.

FIG. 1 generally illustrates a steerable balloon catheter 10 which embodies the present invention and comprises a guidewire tubing or hypotube 12 coupled to a control handle 14. A helical coil 18 is attached to and extends from the distal end of the hypotube 12. The helical coil 18 is of a rectangular, or square, cross-sectional, configuration and is preferably formed from platinum tungsten wire with the proximal turns being wound such that adjacent turns of the proximal portion are in contact, or loosely interlocked, with each other.

While the preferred embodiment of the present invention includes a helical coil 18, this element may take the form of any flexible rectangular, or square cross-sectional member, such as for example a thin square metallic tube with or without portions of the tube removed. An elongated deflection member 20 extends from the proximal end of the control handle through the hypotube 12 and through the helical coil 18, and is connected into an attachment member, or rounded bead 22, which is disposed at the distal tip of the helical coil 18. In addition, a retaining ribbon 24 is connected to the distal end of the hypotube 12 and is also connected to the rounded bead 22.

The control handle 14 generally comprises a slidable control knob 26 which may be moved longitudinally with respect to the control handle. The control handle 14 is coupled to the deflection member 20. As will be discussed in more detail, the longitudinal movement of the slidable control knob 26 causes deflection of the distal tip of the guidewire in either an upward or downward direction.

The steerable balloon catheter 10 also includes an outer cylindrical tubing 27 which surrounds and is in coaxial relationship with the hypotube 12. The inside diameter of the outer cylindrical tubing 27 is slightly larger than the outside diameter of the hypotube 12 so as to form a fluid passageway between the outer tubing 27 and the hypotube 12.

An inflatable balloon 29 which may take the form of an angioplasty balloon, a stent expandable balloon, a perfusion balloon or any other expandable medical balloon, is mounted near the distal end of the outer tubing 27. Also, a side-port connector 27a is positioned between the handle 14 and the outer tubing 27 which serves to provide a port for applying a fluid, such as saline, into the lumen between the outer tubing 27 and the hypotube 12 for inflation of the balloon 29.

Figure 2:
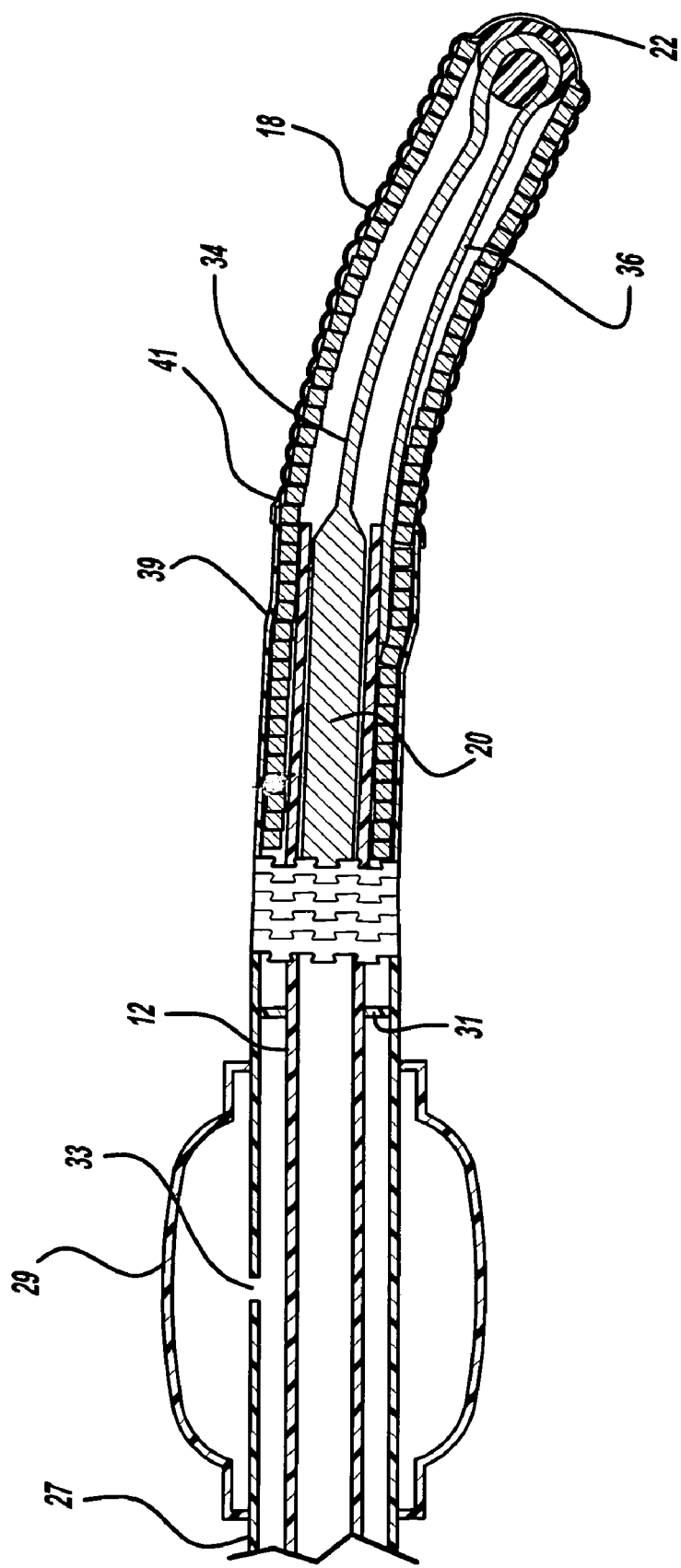
FIG. 2 is an enlarged sectional view showing the distal end of the steerable balloon catheter in its normal pre-shaped position.
Figure 3:
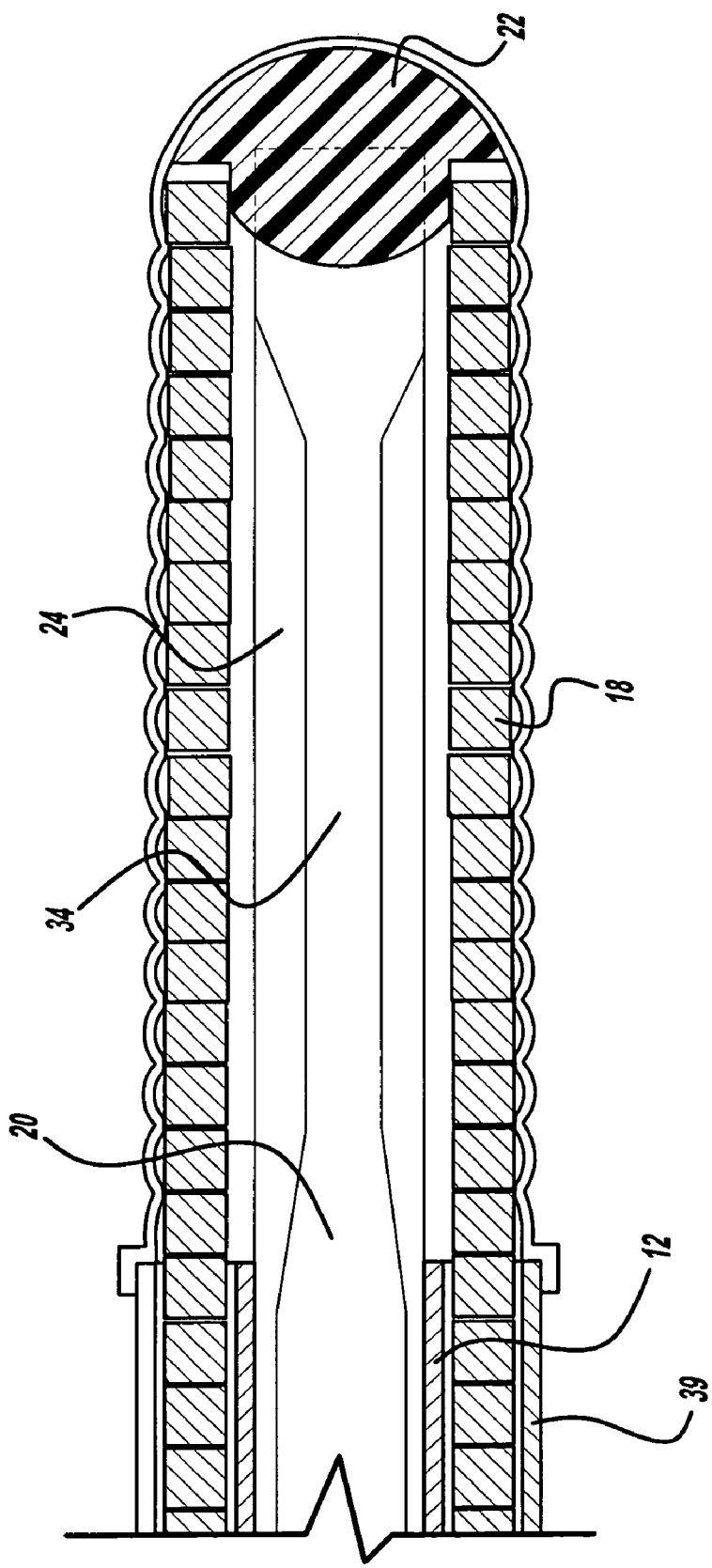
FIG. 3 is an enlarged sectional view showing the distal end of the steerable balloon catheter of FIG. 2 rotated 180 degrees; and, FIGS. 4 and 5 are sectional views showing the steerable balloon catheter deflected from its normal position to opposite extremes of deflection.

FIGS. 2 and 3 illustrate in more detail the distal portion of the hypotube 12. As may be appreciated, FIG. 3 is a view of the hypotube 12 shown in FIG. 2 with the guidewire being rotated 90 degrees about its longitudinal axis. More particularly, the proximal end of the helical coil 18 is bonded, preferably by use of an epoxy, to the outer surface near the distal end of the hypotube 12. The elongated deflection member 20 takes the form of a small diameter cylindrical deflection member 20 having an intermediate portion which is flattened to form a thin deflection ribbon 34 having a thickness of approximately 0.002 inches. The distal end of the cylindrical deflection member 20 is further flattened to a thickness of approximately 0.0015 inches and is bent back 180 degrees to form a U-shaped bend 26a between the deflection ribbon 34 and the retaining ribbon 24. The proximal end of the retaining ribbon 24 is bonded, preferably by use of epoxy, to the outer surface of the distal end of the hypotube 12. The retaining ribbon 24 is aligned in a plane parallel to the plane of the deflection ribbon 34 and the U-shaped portion between the ribbons is encapsulated by the attachment member which preferably takes the form of a rounded epoxy bead 22 bonded to the distal tip of the helical coil 18.

As may be appreciated, with this unitary construction of the ribbon members, these members remain aligned so that both lie in planes parallel to each other. In addition, the U-shaped bend portion when encapsulated into the rounded bead 22 causes the retaining ribbon and deflection ribbon to be properly spaced with respect to each other.

As illustrated in FIG. 2, the retaining ribbon 24 is preferably attached to the rounded bead 22 at a position offset from the center of the bead in the same direction that the retaining ribbon 24 is offset from the longitudinal axis of the hypotube 12. In addition, the deflection ribbon 34 is attached to the bead at a position offset from the center of the bead in an opposite direction from the offset of the retaining ribbon 24.

Also, as may be seen in FIG. 2, the deflection ribbon 34 and the retaining ribbon 24 are pre-shaped into an arcuate, or curved, configuration to thereby maintain the helical coil 18 in a normally curved configuration. The ribbons 24, 34 are pre-shaped such that the distal tip of the steerable balloon catheter curves away from the longitudinal axis of the guidewire in a direction toward that side of the guidewire containing the retaining ribbon 24.

The helical coil 18 is formed as an elongated member having a rectangular, or square, cross-sectional configuration and wound in a helical configuration. In addition, the elongated member is formed with re-occurring steps, or step undulations, which when wound into a helical configuration so that adjacent turns to loosely interlock thereby preventing movement between adjacent turns. Such interlocking turns enhance the rotational rigidity or "torqueability" of the coil such that when the proximal end of the coil is rotated 180 degrees, the distal end of the coil will rotate approximately 180 degrees. Accordingly, the distal end of the coil more nearly tracks, rotationally, the proximal end of the coil thereby significantly improving the "tortional" characteristics of the coil. By improving the "tortional" characteristics of the coil, the overall "tortional" characteristics of the guidewire are significantly improved.

As opposed to winding an elongated member to form the helical coil 18, a preferred method of forming the helical coil is by laser cutting the coil from a single thin-walled tube of an alloy in the undulations locking, stepped configuration as illustrated in FIG. 2. Such laser cutting provides a coil with precise mating surfaces to assure proper interlocking between adjacent turns of the helical coil.

FIG. 2 illustrates in more detail the coaxial relationship between the outer tubing 27 and the hypotube 12 for defining the fluid pathway between these elements. A sealing partition 31 serves to support the distal end of the hypotube 12 within the outer tubing 27 and also serves to seal the distal end of the passageway between these elements. In addition, an opening 33 is provided in the sidewall of the outer tubing 27 which serves to provide a fluid communication between the interior of the balloon and the lumen, and through the lumen to the side port of the fluid connector 27a.

Figure 5:
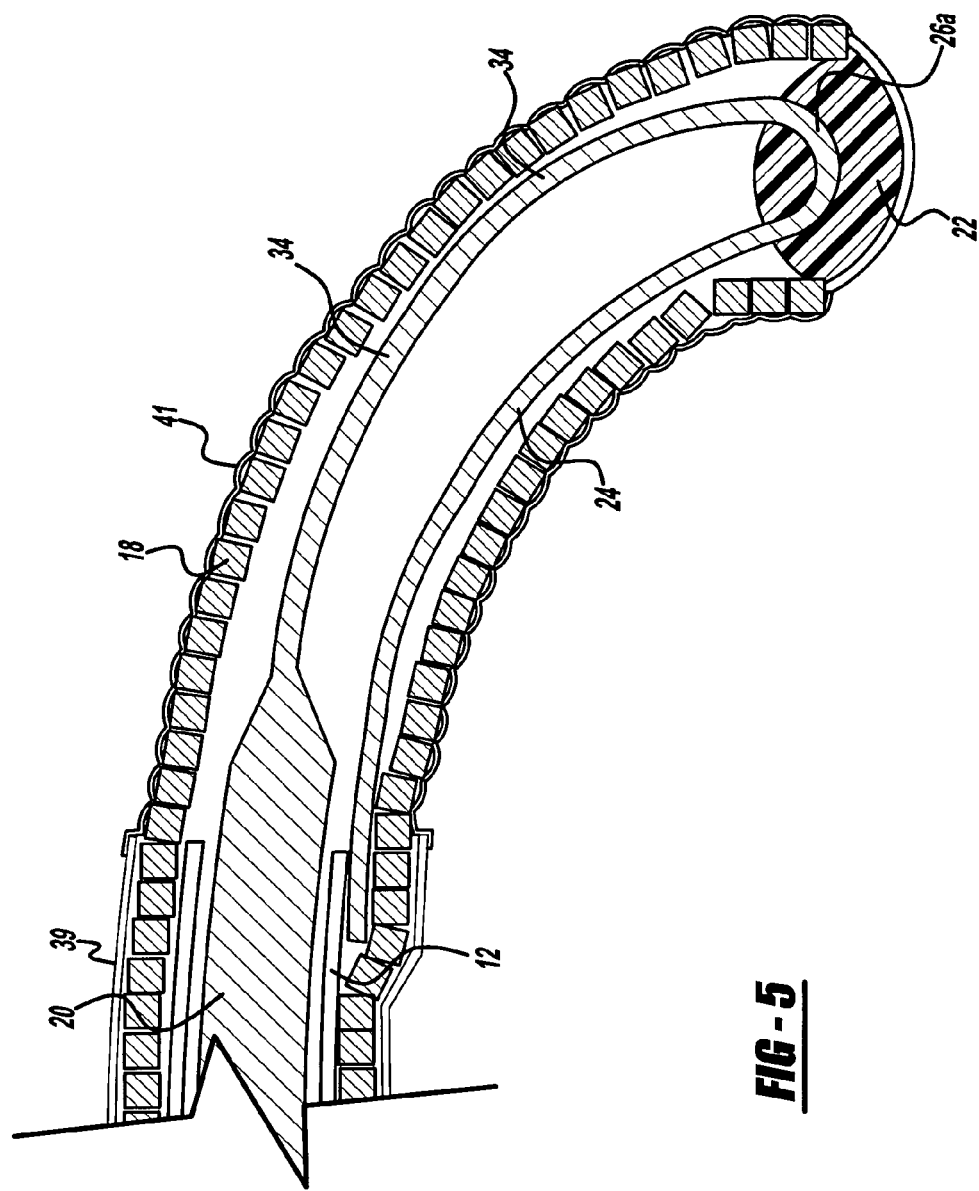

In operation, as previously described, the distal tip of the steerable balloon catheter 10 is normally biased into a downwardly curved position as illustrated in FIG. 2 because of the curve of the pre-shaped deflection ribbon 34 and the retaining ribbon 24. When the slidable control knob 26 is moved distally as shown in FIG. 5, the deflection member 20 will be moved distally thereby causing the deflection ribbon 34 to move in a distal direction. As the deflection ribbon is moved distally, a pushing force is applied to the top portion of the rounded bead 22. The retaining ribbon 24 is attached to the lower portion of the bead 22 to thereby maintain the bead at a fixed distance from the distal end of the hypotube 12. As the deflection ribbon 34 is moved to the right, the distal tip of the steerable balloon catheter is caused to deflect downwardly to a maximum position of deflection.

Since the deflection ribbon 34 and the retaining ribbon 24 are pre-shaped prior to any activation of the steerable guidewire, the amount of force required to deflect the guidewire in this direction is very small thereby preventing buckling of the deflection ribbon 34 as the deflection ribbon is pushed distally. As the deflection ribbon 34 is moved distally, the upper turns of the helical coil become slightly stretched and the lower turns of the coil become slightly compressed. The deflection member 20 has a diameter of about 0.0065 inches and the deflection ribbon has a thickness of about 0.002 inches to thereby provide sufficient stiffness to prevent the buckling of these elements when the deflection member 20 is pushed distally. This construction also provides sufficient stiffness to transmit the necessary force from the proximal end to the distal tip of the steerable balloon catheter.

Figure 4:
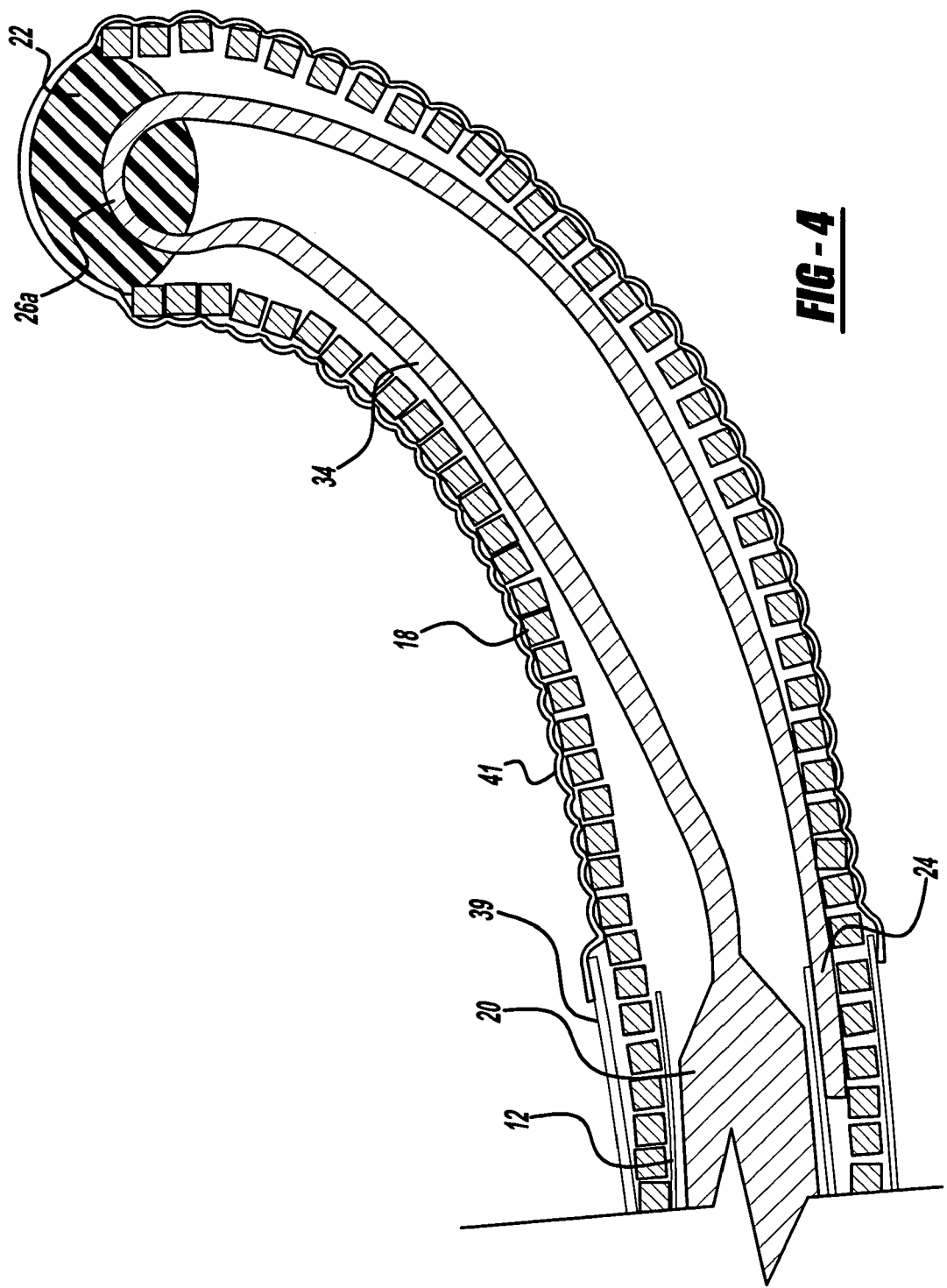

When the slidable control knob 26 is moved in a proximal direction as shown in FIG. 4, the deflection member 20 will be pulled to the left to thereby cause the deflection ribbon 34 to pull on the top portion of the bead 22. Since again the retaining ribbon 24 causes the lower portion of the bead to remain at a fixed distance from the distal end of the hypotube 12, the tip of the steerable balloon catheter 10 is caused to bend in an upward direction to a maximum deflection as shown in FIG. 4. Since the deflection ribbon 34 is in tension when the deflection member 20 is pulled, there is no concern for buckling of the deflection ribbon 34. As the deflection ribbon 34 is moved distally, the lower coil turns become slightly compressed and the upper coil turns become somewhat stretched thereby causing the tip of the steerable balloon catheter to bend downwardly.

As previously discussed, when the proximal end of the hypotube 12 is rotated by a physician to "steer" the distal end of the steerable balloon catheter, with the interlocking turns of adjacent coils of the helical coil 18, the distal tip will rotate on approximately a one-to-one basis with respect to the proximal end of the hypotube 12. In other words, there is only minimal "play" or "lag" between rotation of the proximal end and the distal end of the steerable balloon catheter.

In a preferred embodiment of the present invention, the balloon is preferably formed of a nylon material and, upon inflation, serves to open an occlusion in a vessel or may serve to expand and place a stent within a vessel. The elongated deflection member 20, retaining ribbon 24 and deflection ribbon 34 are constructed of nitinol, but these elements may be formed from other flexible materials including polymers. The helical coil 18 preferably formed by laser cutting as previously discussed, is constructed from an alloy comprised of about 92 percent platinum and 8 percent tungsten, but this element may also be constructed from numerous other materials. It is desirable that the coil exhibit the characteristic of being radiopaque to X-rays to assist in the positioning of the distal tip of the steerable balloon catheter 10. The deflection member 20 is formed from a single cylindrical nitinol wire of about 0.0065 inches in diameter having an intermediate portion which is flattened to form the deflection ribbon 34 with a thickness of about 0.002 inches, and a distal portion which is flattened to form the retaining ribbon 24 with a thickness of about 0.0015 inches. The retaining ribbon 24 is bent back 180 degrees to form a generally U-shaped bend, which is subsequently encapsulated within the rounded bead 22. The rounded bead 22 is preferably formed with epoxy, but may be formed with soldering or by welding.

It has been found that the addition of graphite between the deflection member 20 and deflection ribbon 34, and the inner lumen of the hypotube 12 provides lubrication. Other lubricants, such as Teflon or MDX may be used for this purpose. The helical coil 18 is preferably coated with an elastomeric polymer 41 on its distal end to act as a sealant preventing the entry of blood and contrast media into the guidewire and a fluorinated polymer 39, such as Teflon, on its proximal end for lubrication purposes.

It may be seen that the balloon on a guidewire as disclosed may be very easily and very precisely rotated and then deflected in either of two directions for very precise steering of the steerable balloon catheter through the vessels of the body. As may be apparent, the disclosed steerable balloon catheter may be used to perform angioplasty or it may be used to position and place a stent within a vessel of the body.

The preceding specific embodiment is illustrated of the practice of this invention. It is to be understood, however, that other variations may also be employed without departing from the spirit and scope of the invention as hereinafter claimed.

That which is claimed is:

1. A steerable balloon catheter having a deflectable tip which comprises:

an inner elongated flexible hollow tubing having proximal and distal portions;

a flexible helical coil having proximal and distal ends, the proximal end of said helical coil is attached to the distal portion of the inner elongated flexible hollow tubing;

an elongated deflection member having proximal and distal portions and being slidably disposed within said inner elongated flexible hollow tubing and within said helical coil, the distal portion of said deflection member being flattened to form a deflection ribbon which extends in a plane;

a retaining ribbon having proximal and distal ends, the proximal end of the retaining ribbon is attached to the distal portion of the inner elongated flexible hollow tubing and the retaining ribbon is oriented to extend in a plane which is generally parallel to the plane of the deflection ribbon;

an attachment member engaging the distal end of the helical coil, the distal portion of the deflection member, and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction;

the attachment member takes the form of a rounded bead which contacts the distal end of the helical coil to define a curved surface at the distal end of the coil;

the deflection ribbon engages the rounded bead at a location offset from the center of the curved surface of the rounded bead;

the distal end of the retaining ribbon engages the rounded bead at a location offset from the center of the curved surface of the rounded bead;

said deflection ribbon and said retaining ribbon being joined together to form a generally U-shaped configuration;

an outer elongated flexible tubing surrounding the inner elongated hollow tubing so as to define a passageway between the outer tubing and the inner elongated flexible hollow tubing; and an inflatable balloon mounted on the outer flexible tubing and communicating with the passageway between the outer tubing and the inner hollow tubing.

2. A steerable balloon catheter as defined in claim 1, wherein the retaining ribbon and the deflection ribbon are normally biased in an arcuate configuration to thereby cause the distal end of the helical coil to be normally biased in a curved shape.

3. A steerable balloon catheter as defined in claim 1, wherein the proximal portion of said deflection member is of a circular cross section which extends from the proximal portion of the inner flexible tubing to approximately the distal portion of the inner flexible tubing.

4. A steerable balloon catheter as defined in claim 3, wherein the proximal end of said retaining ribbon extends from the distal portion of the inner flexible tubing to approximately the distal end of the flexible helical coil.

5. A steerable balloon catheter as defined in claim 1, wherein the rounded bead is formed with an epoxy material.

6. A steerable balloon catheter as defined in claim 1, wherein the distal end of the retaining ribbon engages the rounded bead at a location offset from the center of the circular surface in an opposite direction from the offset location of the deflection ribbon.

7. A steerable balloon catheter as defined in claim 6, wherein the deflection member and the retaining ribbon are joined to each other within the rounded bead.

8. A steerable balloon catheter as defined in claim 7, wherein the deflection ribbon and the retaining ribbon are formed as a single unitary element.

9. A steerable balloon catheter as defined in claim 1, wherein the deflection ribbon and the retaining ribbon provide a predetermined spacing between the deflection ribbon and the retaining ribbon and to maintain the deflection ribbon and the retaining ribbon in planes which are parallel to each other.

10. A steerable balloon catheter as defined in claim 1, wherein the deflection ribbon is formed by flattening an intermediate portion of the deflection member and the retaining ribbon is formed by flattening the distal portion of the deflection member.

11. A steerable balloon catheter as defined in claim 10, wherein the retaining ribbon is of a thickness which is less than the thickness of the deflection ribbon.

12. A steerable balloon catheter as defined in claim 11, wherein the deflection ribbon is of a thickness equal to about 0.002 inches and the retaining ribbon is of a thickness equal to about 0.0015 inches.

13. A steerable balloon catheter having a deflectable tip which comprises:

an inner elongated flexible hollow tubing having proximal and distal portions;

a flexible helical coil having proximal and distal ends, the proximal end of said helical coil is attached to the distal portion of the inner elongated flexible hollow tubing;

an elongated deflection member having proximal and distal portions and being slidably disposed within said hollow tubing and within said helical coil, the distal portion of said deflection member being tapered;

an elongated retaining member having proximal and distal ends, the proximal end of the retaining member is attached to the distal portion of the flexible hollow tubing;

an attachment member engaging the distal end of the helical coil, the deflection member, and the distal end of the retaining member so that longitudinal movement of the deflection member in a distal direction causes the distal end of the helical coil to be deflected in one direction and longitudinal movement of the deflection member in a proximal direction causes the distal end of the helical coil to deflect in an opposite direction;

said retaining member being preshaped into an arcuate configuration to thereby cause the flexible helical coil to be normally biased into a curved shape;

an outer elongated flexible tubing surrounding the inner elongated hollow tubing so as to define a passageway between the outer elongated flexible tubing and the inner elongated hollow tubing; and, an inflatable balloon mounted on the outer elongated tubing and the communicating with the passageway between the outer tubing and the inner tubing.

14. A steerable balloon catheter as defined in claim 13, wherein the attachment member takes the form of a rounded bead.

15. A steerable balloon catheter as defined in claim 13, wherein a portion of the attachment member extends across the distal end of the helical coil, the distal portion of the deflection member engages the attachment member at a location offset from the center of the attachment member extending across the distal end of the helical coil.

16. A steerable balloon catheter as defined in claim 15, wherein the distal end of the retaining member engages the attachment member at a location offset from the center of the attachment member extending across the distal end of the helical coil.

17. A steerable balloon catheter as defined in claim 16, wherein the distal end of the retaining member engages the attachment member at a location offset from the center of the attachment member in an opposite direction from the offset location of the deflection member.

18. A steerable balloon catheter as defined in claim 13, wherein the deflection member and the retaining member are joined to each other within the attachment member.

19. A steerable balloon catheter as defined in claim 18, wherein the deflection member and the retaining member are formed as a single unitary element.

20. A steerable balloon catheter as defined in claim 19, wherein the junction between the deflection member and the retaining member form a generally U-shaped configuration to thereby provide a predetermined spacing between the distal portion of the deflection member and the distal end of the retaining member.

21. A steerable balloon catheter as defined in claim 20, wherein the attachment member takes the form of a rounded bead.

22. A steerable balloon catheter having a deflectable tip which comprises:

a first elongated flexible hollow tubing having proximal and distal portions;

a flexible helical coil having proximal and distal ends, the proximal end of said helical coil is attached to the distal portion of the first elongated flexible hollow tubing;

an elongated deflection member comprised of proximal and distal portions and being slidably disposed within said hollow tubing and within said helical coil, the proximal portion of the deflection member being of a cylindrical cross section and the distal portion of said deflection member takes the form a deflection ribbon which extends in a plane;

a retaining ribbon having proximal and distal ends, the proximal end of the retaining ribbon is attached to the distal portion of the first elongated flexible hollow tubing and the retaining ribbon is oriented to extend in a plane which is generally parallel to the plane of the deflection ribbon;

an attachment member engaging the distal end of the helical coil, the distal portion of the deflection member, and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction;

wherein the attachment member takes the form of a rounded bead which contacts the distal end of the helical coil to define a curved surface at the distal end of the coil, and the deflection ribbon engages the rounded bead at a location offset from the center of the rounded surface of the rounded bead; and wherein the distal end of the retaining ribbon engages the rounded bead at a location offset from the center of the rounded surface of the rounded bead, said retaining ribbon being offset from the center of the rounded surface in an opposite direction from the offset location of the deflection ribbon; said deflection ribbon and retaining ribbon being joined to each other within the rounded bead;

a second elongated flexible tubing attached to and supported by said first elongated flexible hollow tubing, said second tubing having an inflation lumen; and an inflatable balloon mounted on said second elongated flexible tubing and communicating with the lumen of said second elongated tubing.

23. A steerable balloon catheter as defined in claim 22, wherein the retaining ribbon and the deflection ribbon are normally biased in an arcuate configuration to thereby cause the distal end of the helical coil to be normally biased in a curved shape.

24. A steerable balloon catheter as defined in claim 22, wherein the distal portion of the deflection member and the deflection ribbon are formed from a wire of a circular cross section and in which the distal portion is flattened to form a deflection ribbon.

25. A steerable balloon catheter as defined in claim 22, wherein the deflection ribbon and the retaining ribbon are joined to form a generally U-shaped configuration to thereby provide a predetermined spacing between the deflection ribbon and the retaining ribbon and to maintain the deflection ribbon and the retaining ribbon in planes which are parallel to each other.

26. A steerable balloon catheter as defined in claim 25, wherein the deflection ribbon is formed by flattening an intermediate portion of the deflection member and the retaining ribbon is formed by flattening a distal portion of the deflection member.

27. A steerable balloon catheter as defined in claim 26, wherein the retaining ribbon is of the thickness which is less than the thickness of the deflection ribbon.

28. A steerable balloon catheter as defined in claim 22, wherein the proximal portion of the elongated flexible tubing is coupled to a control handle and the elongated deflection member is mounted with the control handle for longitudinal movement.

29. A steerable balloon catheter as defined in claim 28, wherein said control handle includes a movable knob which is coupled to the elongated deflection member for longitudinal positioning of the deflection member.

30. A steerable balloon catheter as defined in claim 29, wherein said control handle is coupled to the elongated flexible tubing with a release mechanism so that the handle may be removed from the guidewire.

* * * * *